US008268248B2

(12) United States Patent
Steuerwald et al.

(10) Patent No.: US 8,268,248 B2
(45) Date of Patent: Sep. 18, 2012

(54) ONLINE ANALYZER

(75) Inventors: Ralf Steuerwald, Welzheim (DE); Dirk Steinmueller, Karlsruhe (DE); Camiel Heffels, Ditzingen (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 1496 days.

(21) Appl. No.: 10/515,306

(22) PCT Filed: May 17, 2003

(86) PCT No.: PCT/EP03/05208
§ 371 (c)(1),
(2), (4) Date: Aug. 2, 2005

(87) PCT Pub. No.: WO03/098198
PCT Pub. Date: Nov. 27, 2003

(65) Prior Publication Data
US 2006/0051238 A1 Mar. 9, 2006

(30) Foreign Application Priority Data
May 21, 2002 (DE) .................................. 102 22 822

(51) Int. Cl.
*G01N 21/00* (2006.01)
(52) U.S. Cl. ................................................. 422/82.05
(58) Field of Classification Search ................. 422/82.05
See application file for complete search history.

(56) References Cited

U.S. PATENT DOCUMENTS

| 3,560,161 A | * | 2/1971 | Webb ............................. 422/81 |
| 4,820,045 A | * | 4/1989 | Boisde et al. ................. 356/319 |
| 5,042,893 A | * | 8/1991 | Ong ................................ 385/49 |
| 5,173,749 A | * | 12/1992 | Tell et al. ..................... 356/437 |
| 5,537,336 A | * | 7/1996 | Joyce ............................ 702/108 |
| 5,569,911 A | | 10/1996 | Tomlinson, Jr. |
| 6,277,330 B1 | | 8/2001 | Liu |
| 6,542,231 B1 | * | 4/2003 | Garrett ......................... 356/246 |

FOREIGN PATENT DOCUMENTS

| DE | G 93 19 750.0 | 3/1994 |
| DE | 200 03 082 U1 | 8/2000 |

(Continued)

OTHER PUBLICATIONS

Machine English Translation of JP 05-172830. Date of translation: Jul. 11, 2008.*

(Continued)

*Primary Examiner* — Bobby Ramdhanie
(74) *Attorney, Agent, or Firm* — Bacon & Thomas, PLLC

(57) ABSTRACT

An on-line analyzer for analyzing a test sample, having a measuring device, which includes at least one measuring cell and at least one optoelectronic component. The measuring device determines, at at least one wavelength, the transmission or absorption of electromagnetic radiation passing through the test sample and provides measurement signals. The analyzer further includes a control/evaluation unit, which evaluates the measurement signals delivered by the measuring device and makes analysis data available. The measuring cell and the control/evaluation unit are located spatially separated from one another; the at least one optoelectronic component of the measuring device is assigned to the control/evaluation unit; the measuring cell and the at least one optoelectronic component are connected together via a light wave conductor.

13 Claims, 2 Drawing Sheets

FOREIGN PATENT DOCUMENTS

| | | | |
|---|---|---|---|
| DE | 19952652 A1 | * | 4/2001 |
| DE | 100 63 024 A1 | | 8/2001 |
| GB | 2 298 712 A | | 9/1996 |
| JP | 05172830 | * | 7/1993 |
| WO | WO 99/47261 | | 9/1999 |

OTHER PUBLICATIONS

DE 19824652 Abstract, Date: Feb. 12, 1999.
DE 19615957 Abstract, Date: Oct. 23, 1997.
DE 4116431 Abstract, Date: Nov. 19, 1992.
DE 2630645 Abstract, Date: Sep. 27, 1978.
EP 0157310 Abstract, Date: Jun. 21, 1988.
EP 0109536 Abstract, Date: Aug. 11, 1987.
DE 19952652 Abstract, Date: Apr. 26, 2001.
DE 3538626 Abstract, Date: Apr. 30, 1986.
DE 3637161 Abstract, Date: May 14, 1987.
DE 3403372 Abstract, Date: Jul. 25, 1985.
Japanese application 03292095 Abstract, Date: Jul. 13, 1993.

* cited by examiner

ONLINE ANALYZER

FIELD OF THE INVENTION

The invention relates to an on-line analyzer for analyzing a test sample.

BACKGROUND OF THE INVENTION

On-line analyzers are marketed by the Endress+Hauser Conducta GmbH +Co., KG under the trademark "STAMOLYS". The analyzers are used in, among other things, the monitoring and optimizing of cleaning performance of a clarification plant, the monitoring of aeration tanks and clarification plant effluent, or the control of filler dosing. Examples of parameters measured and monitored include the concentration of ammonium, phosphate or nitrate in a test sample. The analysis of a test sample occurs on the basis of known measuring methods that do not need to be gone into in greater detail here.

On-line analyzers register daily information preferably continuously as a function of time. They deliver, on the one hand, desired information reliably with respect to the ongoing operation of the plant; on the other hand, information respecting possibly required changes in the process technology are furnished. On the basis of the analysis data, it is possible at times to achieve quite considerable savings in operating means and operating costs.

The working procedure in an on-line analyzer containing a calorimetric measuring device is roughly as follows: a pump fills the permeate—thus, the collected test sample - into a mixing container. A reagents pump feeds to the test sample a suitable reagent in a specified mixing ratio. The reagent reacts with the test sample, whereby the test sample turns color in a characteristic manner. A measurement of the absorption or transmission of radiation directed through the reacted test sample is determined by means of a photometer or a spectrometer. The absorption, or transmission, as the case may be, delivers information on the concentration of a chemical element or a chemical compound in the test sample. Preferably, the temperature of the photometer in the STAMOLYS analyzer is controlled thermostatically, in order that the intended reaction between permeate and reagent can proceed reproducibly and be completed within a short time.

In the case of known analyzers, the photometer with measuring cell, together with the pumps for supply of permeate, reagent and/or cleaning agent, and the valves for switching between internal cycles (calibration, cleaning), are all accommodated on one mounting frame. Consequently, the electronics for amplifying the optical signals of the optoelectronic components, e.g. the photodiodes, are located in the so-called wet part of the on-line analyzer. In order to protect the sensitive optoelectronic components of the photometer, or spectrometer, as the case may be, against wetness and electromagnetic interference, it is absolutely necessary in the known instances to accommodate the electronics in a separate, sealed, protective housing. In general, the known solution involves relatively many individual components: On the one hand, its assembly is rather complex; on the other hand, the space requirement for the known solution is relatively large.

SUMMARY OF THE INVENTION

An object of the invention is to provide an on-line analyzer, in which the wet part and the electronics part are completely decoupled from one another.

The analyzer of the invention includes a measuring device, which determines the transmission or the absorption of electromagnetic radiation of at least one wavelength as it passes through the test sample, and provides the measurement signal, and a control/evaluation unit, which evaluates the measurement signal delivered by the measuring device and makes analysis data available. The measuring device includes at least one measuring cell and at least one optoelectronic component. Measuring cell and control/evaluation unit are located spatially separated from one another. The at least one optoelectronic component of the measuring device is assigned to the control and evaluation unit. Additionally, at least one light wave conductor, such as a fiber optic connection, is provided, over which the measuring cell and the at least one optoelectronic component are connected with one another.

By way of the invention, it is thus possible, for the first time, to separate spatially, and decouple completely, from the optoelectronic and electrical components, all components of the analyzer that come into direct contact with the test sample. Especially, in the case of use of a photometer, the sensitive electronics for amplifying the optical measurement signals of the photodiodes are situated outside of the wet part of the analyzer. In this way, a damaging of the sensitive electronic parts in the case of a burst hose is reliably avoided. Moreover, the on-line analyzer of the invention has excellent EMC-properties.

Preferably, the measuring device is a single channel or a plural-channel photometer. However, a spectrometer can also be used for the on-line analyzer of the invention.

The optoelectronic components can be light-emitting diodes, a photodiode or a diode-array spectrometer.

In an advantageous further development of the on-line analyzer of the invention, at least one plug-connector is provided, via which the at least one optoelectronic component is connectable with the light wave conductor. In addition to this, an embodiment with plural light wave conductors is provided, wherein the light wave conductors are collected in a light wave conductor bundle. This embodiment provides an orderly arrangement of the light wave conductors.

In the case of a two-channel photometer, two light wave conductors are used, with one light wave conductor, or channel, for the measuring wavelength and one light wave conductor, or channel, for the reference wavelength.

In the case of a diode-array spectrometer, a fiber optic light coupler is provided, via which the optoelectronic components of the spectrometer and the light wave conductors are connected together. Using the light wave conductor technology, it is possible, instead of colored light-emitting diodes or photodetectors, to use a broadband light source for illumination of the measuring cell. For the spectrally resolved measurement, a diode-array spectrometer with fiber optic light coupling is, as already indicated, made use of. In these ways, the different measured variables of a test sample can be determined with one piece of hardware. Additionally, some measured variables in the UV/VIS or NIR spectral regions can be measured directly, thus without reagents.

A preferred further development of the analyzer of the invention provides that the optoelectronic components and the electronic and/or electrical components of the measuring device and/or of the analyzer are located on at least one circuit board. Especially, it is provided that all optoelectronic components are located on the main board, on which the components of the amplification electronics are also to be found. This practice leads to reduction of manufacturing costs.

Additionally in connection with the analyzer of the invention, at least one pump unit is provided, via which the test sample and/or a reagent and/or cleaning agent is introduced into the measuring cell. According to one form of embodiment, the control/evaluation unit assumes complete control of the operation of the on-line analyzer. Preferably, the control/evaluation unit, the so-called electronics part, is located in the upper region and/or in the back region of the on-line analyzer; additionally, at least one dividing wall is provided, which separates the electronics part from the wet part, where, among other things, the measuring cell and/or the pump unit are/is to be found. Since the electronics part is now well sealed-off from the wet part, the previously required, separate, protective housing for the sensitive electronic parts of the photometer can be omitted.

The invention will now be explained in greater detail on the basis of the drawings, the figures of which show as follows:

DESCRIPTION OF THE PREFERRED EMBODIMENT

Figure 1:
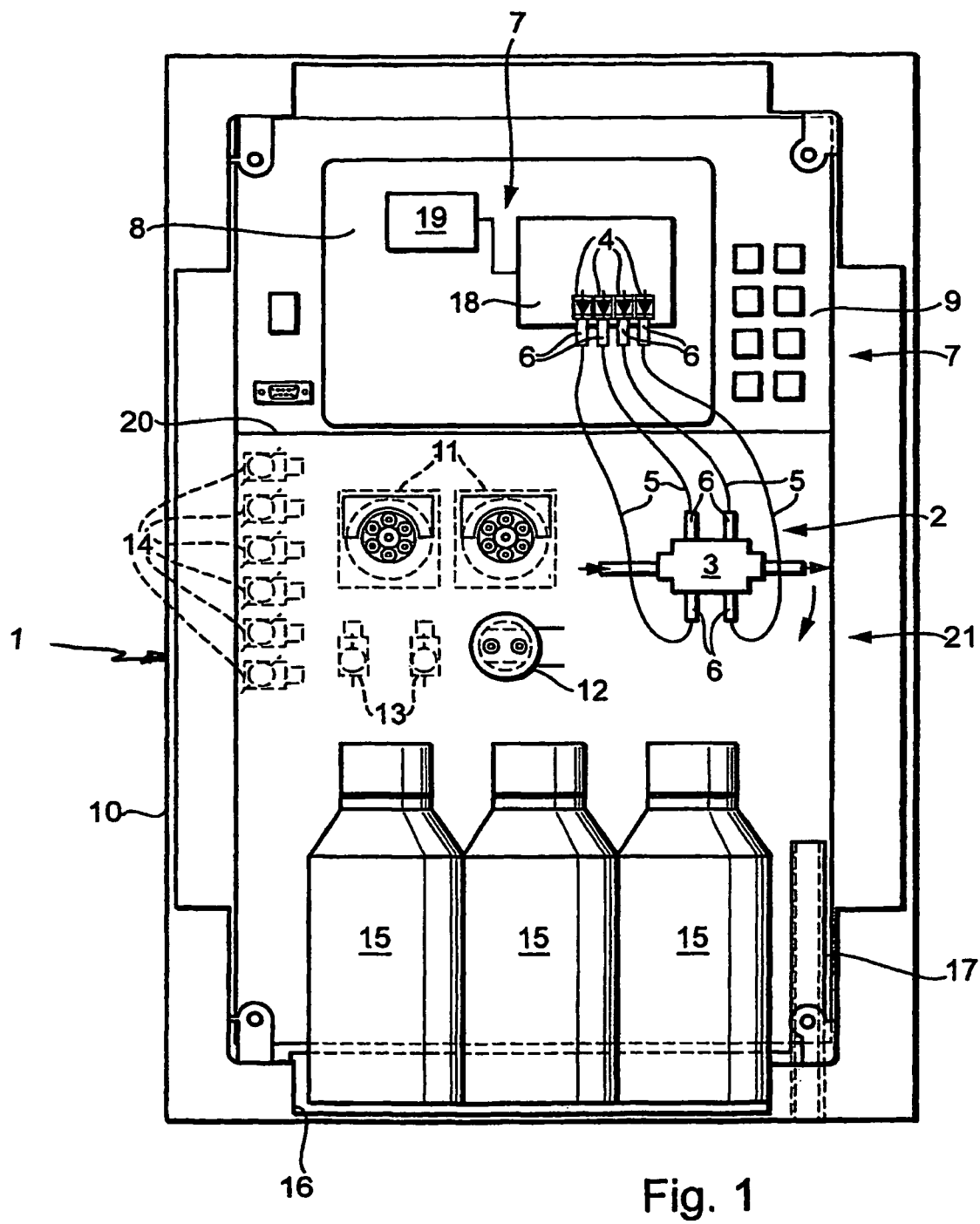
FIG. 1: is a front view of an on-line analyzer of the invention.
Figure 2:
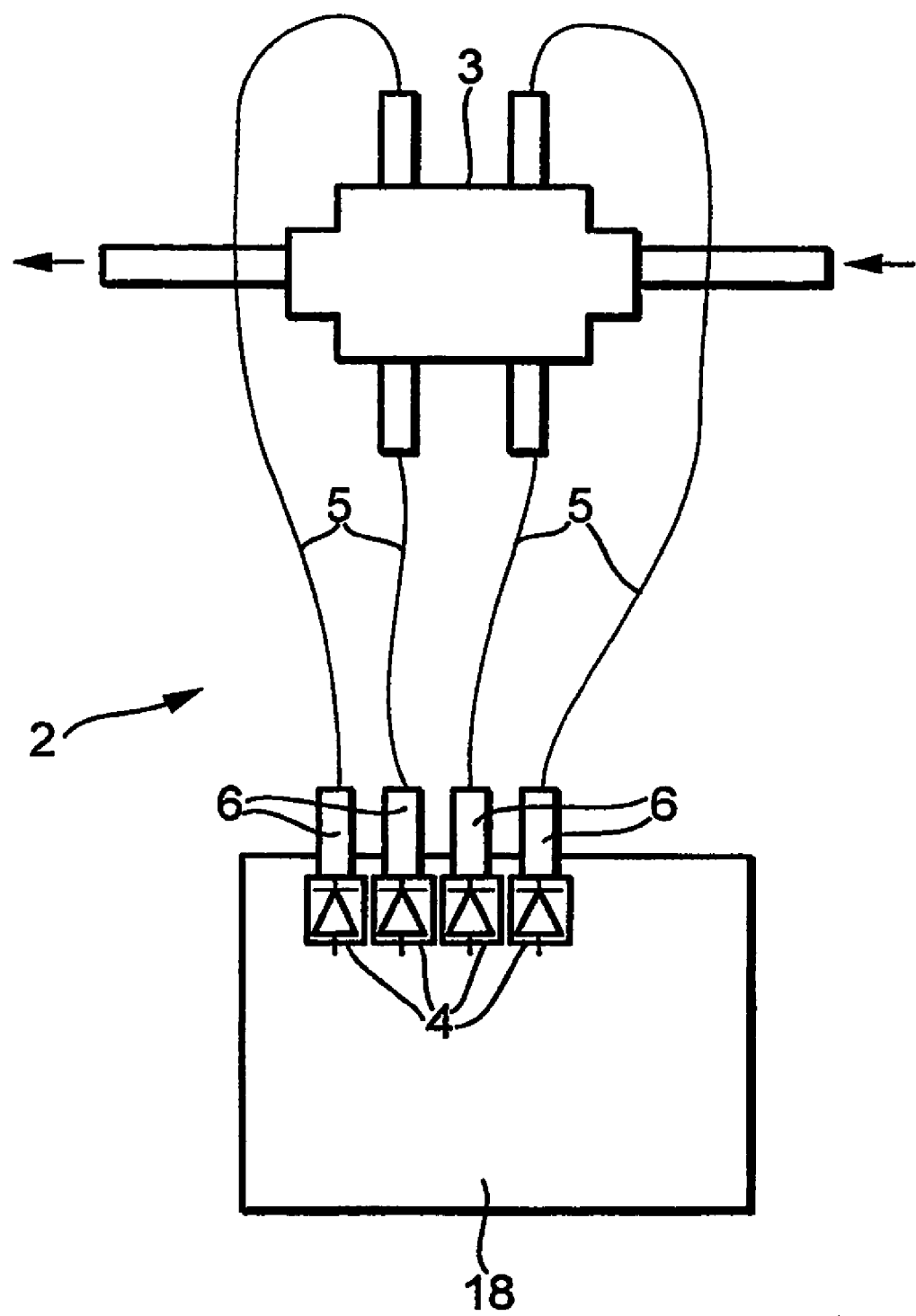
FIG. 2: is a view of the embodiment of the measuring device component of FIG. 1.

Housing 10 of the on-line analyzer 1 of the invention is separated by dividing wall 20 into an electronics part 7 and a wet part 21. In the illustrated example, dividing wall 20 is arranged horizontally and separates the electronics part 7, located in the upper region of housing 10, from the wet part 21, located in the lower part of the housing 10. In the wet part 21 are found all components of the on-line analyzer 1 that come in direct contact with the liquid test sample. In the illustrated case, these are the channel switching valves 14, the pumps 11, the shut-off valves 13, the dosing loop 12, the measuring cell 3 and the receptacles 15.

The measuring device 2 includes a measuring cell 3 and a plurality of optoelectronic components 4. While the measuring cell 3 is to be found in the wet part 21 of the on-line analyzer, the optoelectronic components 4 are located in the electronics part 7. The measuring cell and the optoelectronic components 4 are, according to the invention, connected via light wave conductors 5. The light wave conductors 5 and the optoelectronic components 4, same as for the light wave conductors 5 and the measuring cell 3, are connected together using plug connectors 6. By this feature, it is possible, for example, to perform a simple exchanging of a measuring cell 3 in favor of another measuring cell 3 of different thickness. Of course, the light wave conductors 5 can also be connected permanently with the optoelectronic components 4 or the measuring cell 3. The illustrated case also concerns a so-called two-channel photometer: The measuring and reference beams are coupled in, and out, via separate light conductors 5.

Also located in the electronics part 7 is the control/evaluation unit 19, which is responsible for the sequence control of the on-line analyzer 1 and for the evaluation and for the providing of the analysis data. Both the sequence control and the winning of the measured values are subjects already known in the state of the art, so that a detailing of these subjects will not be made here. Preferably, all electronic and electrical components 4, 19 are located on a single board 18.

In the lower region of the wet 21 are located the receptacles 15, for storage of reagents and cleaning agents. The reacted test samples and used cleaning agents are discharged through the outlet tube 17.

The invention claimed is:

1. An on-line analyzer for analyzing a test sample, having:
a measuring device comprising at least one measuring cell and at least one optoelectronic component, said measuring device determines, at at least one wavelength, a transmission or an absorption of electromagnetic radiation passed through the test sample;
a control/evaluation unit, which evaluates the measurement signals delivered by said measuring device;
at least one light wave conductor;
a pump unit via which the test sample and/or a reagent are/is supplied into said measuring cell; and
at least one dividing wall, which separates and decouples completely an electronics components part from a wet part, wherein:
said at least one measuring cell and said control/evaluation unit are located spatially separated from one another with at least said at least one measuring cell and said pump unit being arranged in said wet part and said at least one control/evaluation unit and said at least one optoelectronic component being located in said electronics components part;
said at least one optoelectronic component is assigned to said control/evaluation unit; and
said at least one light wave conductor is provided, via which said at least one measuring cell and said at least one optoelectronic component are connected together.

2. The on-line analyzer as claimed in claim 1, wherein:
said measuring device comprises one of a one-channel and a plural-channel photometer.

3. The on-line analyzer as claimed in claim 1, wherein:
said measuring device comprises a spectrometer.

4. The on-line analyzer as claimed in claim 1, wherein:
said optoelectronic component comprises one of: a light-emitting diode, a photodiode and a diode-array spectrometer.

5. The on-line analyzer as claimed in claim 1, further having:
at least one plug-connector, via which said optoelectronic component is connectable with said light wave conductor.

6. The on-line analyzer as claimed in claim 1, wherein:
a plurality of light wave conductors is provided, collected together in a light wave conductor bundle.

7. The on-line analyzer as claimed in claim 2, wherein:
in the case of a two-channel photometer, two light wave conductors are used,
with one channel provided for the measuring wavelength and one channel for the reference wavelength.

8. The on-line analyzer as claimed in claim 3, wherein:
in the case of a diode-array spectrometer, a fiber optic light coupler is provided, via which said optoelectronic components and said light wave conductors are connected together.

9. The on-line analyzer as claimed in claim 1, wherein:
said optoelectronic components and the electronic and/or electrical components of said measuring device and/or of the analyzer are arranged on a circuit board.

10. The on-line analyzer as claimed in claim 1, wherein:
said control/evaluation unit directs sequential control of the on-line analyzer.

11. An on-line analyzer for analyzing a test sample comprising:
a measuring device comprising at least one measuring cell and at least one optoelectronic component;
a control/evaluation unit, which evaluates signals delivered by said measuring device at least one light wave conductor, via which said measuring cell and said optoelectronic component are connected;

a pump unit via which a test sample and/or a reagent are/is supplied into said measuring cell, a housing, which is separated by a dividing wall into an electronics part and a wet part, which are separated and completely decoupled from one another, wherein said control/evaluation unit and said at least one optoelectronic component are located in said electronics components part and wherein said measuring cell and said pump unit are arranged in said wet part.

12. The on-line analyzer as claimed in claim 11, wherein:
said dividing wall is arranged horizontally and separates said electronics part located in an upper region of said housing from said wet part located in a lower part of said housing.

13. The on-line analyzer as claimed in claim 11, wherein:
in the wet part are arranged all components of said on-line analyzer that come into contact with said test sample and/or said reagent.

* * * * *